United States Patent [19]

Hamilton

[11] Patent Number: 4,947,861

[45] Date of Patent: Aug. 14, 1990

[54] NONINVASIVE DIAGNOSIS OF GASTRITIS AND DUODENITIS

[76] Inventor: Lyle H. Hamilton, 1034 N. 124th Street, Wauwatosa, Wis. 53226

[21] Appl. No.: 345,843

[22] Filed: May 1, 1989

[51] Int. Cl.$^5$ ............................................. A61O 5/08
[52] U.S. Cl. .................................. 128/719; 128/730; 128/898
[58] Field of Search ............... 128/632, 636, 716, 719, 128/730, 897, 898

[56] References Cited

U.S. PATENT DOCUMENTS

| | | | |
|---|---|---|---|
| 2,795,223 | 6/1957 | Stampe | 128/730 |
| 3,303,840 | 2/1967 | Etzlinger | 128/730 |
| 3,426,745 | 2/1969 | Farr | 128/730 |
| 3,544,273 | 12/1970 | McConnaughey | 128/730 |
| 3,734,692 | 5/1973 | Lucker et al. | 120/730 |
| 3,777,571 | 12/1973 | Jaeger | 128/730 |
| 3,858,573 | 1/1975 | Ryan et al. | 128/730 |
| 4,579,826 | 4/1986 | Bolton et al. | 128/730 |
| 4,646,786 | 3/1987 | Williams | 128/730 |
| 4,821,737 | 4/1989 | Nelson | 128/730 |

FOREIGN PATENT DOCUMENTS 2497686 7/1982 France ................................. 128/730

OTHER PUBLICATIONS

Coelho et al., "Campylobacter pylori in Esophagus, Antrum, and Duodenum", *Digestive Diseases and Sciences*, vol. 34, No. 3 (Mar. '89), p. 445.

Bartlett "Campylobacter pylori, Fact or Fancy", *GAstroenterology*, vol. 94, No. 1 (Jan., '88), p. 229.

Evans et al., "A Sensitive and Specific Serologic Test for Detection of Campylobacter pylori Infection", *Gastroenterology*, Apr., 1989, p. 1004.

Graham et al., "Campylobacter Pylori Detected Noninvasively by the 13C-Urea Breath Test", *The Lancet*, May 23, 1987, p. 1174.

"C-Urea Breath Analysis, A Non-Invasive Test for Campylobacter Pylori in the Stomach", The Lancet, Jun. 13, 1987, p. 1367.

*Primary Examiner*—Randall L. Green
*Assistant Examiner*—K. M. Reichle
*Attorney, Agent, or Firm*—Nilles & Nilles, S.C.

[57] ABSTRACT

A patient to be treated for the presence of *Campylobacter pylori* in the stomach and/or duodenum ingests a quantity of urea and after about 10 minutes exhales into breath collection apparatus to provide a breath sample of alveolar air, collected during the last part of the exhalation. Immediately upon issuing from the patient the expired breath is passed in contact with a preferably solid-state body of alkaline hygroscopic material, e.g. sodium hydroxide, that substantially removes water vapor from the breath but is inert to ammonia in the presence of water. The breath sample, thus dehydrated, is delivered to a sensor which signals the presence of ammonia in it, to indicate presence of *C. pylori* in the stomach.

9 Claims, 2 Drawing Sheets

NONINVASIVE DIAGNOSIS OF GASTRITIS AND DUODENITIS

FIELD OF THE INVENTION

This invention relates to a method and apparatus for noninvasive diagnosis of gastritis and duodenitis, and the invention is more particularly concerned with a method and apparatus for detecting trace quantities of ammonia in the exhaled breath of a patient who has previously ingested a small quantity of urea.

BACKGROUND OF THE INVENTION

It is a relatively recent discovery that a colony of *Campylobacter pylori* bacteria is usually found associated with gastritis and duodenitis, and is frequently found at the sites of peptic and duodenal ulcers. (Coelho et al: "*Campylobacter pylori* in Esophagus, Antrum, and Duodenum", Digestive Diseases and Sciences, Vol. 34, No. 3 (Mar. '89), p. 445; Bartlett: "*Campylobacter pylori*, Fact or Fancy", Gastroenterology, Vol. 94, No. 1 (Jan., '88), p. 229). Suitable medication for combating the bacteria is known, but it is important that there be a reliable test for its presence so that proper treatment is assured, progress of the treatment can be monitored, and methods of eradication can be assessed.

Heretofore the most frequently employed technique for determining the presence of *C. pylori* and disease conditions associated with it has involved the insertion of an endoscope into the stomach, after administration of a suitable sedative to the patient, for direct visual examination of the gastric mucosa tract and/or withdrawal of a biopsy specimen. This procedure required a high degree of skill on the part of the person performing it, subjected the patient to some risk of injury, and was in any case uncomfortable for the patient. Thus a noninvasive technique for diagnosing ulcer or determining the presence of *C. pylori* is very much desired, as pointed out by Bartlett, supra, and by Evans et al: "A Sensitive and Specific Serologic Test for Detection of *Campylobacter pylori* Infection", Gastroenterology, Apr., 1989, p. 1004.

Graham et al reported successful results with a breath test wherein patients first ingested urea labelled with carbon-13 a stable, naturally occurring non-radioactive isotope. In the presence of urea, *C. pylori* produces urease, an enzyme that breaks down urea into ammonia, carbon dioxide and other products. Graham et al found that for persons confirmed by other tests to have *C. pylori* infections, $^{13}CO_2$, derived from the labelled urea, was present in the breath in readily detectable and substantially constant quantities during the period from about 20 minutes to about 100 minutes after the ingestion of the urea; whereas little or none of the labelled $CO_2$ was found in the breaths of persons confirmed as free of *C. pylori*. ("Campylobacter Pylori Detected Noninvasively by the $^{13}C$-Urea Breath Test," The Lancet, May 23, 1987, p. 1174).

A major disadvantage of the technique employed by Graham et al is that detecting the presence of the isotopic $CO_2$ requires the use of a complicated and expensive mass spectrometer, which is not available to many hospitals and is unlikely to be found in a clinic, much less in an individual physician's office.

Bell et al reported successful use of a generally similar technique wherein the ingested urea was labelled with carbon-14, which is radioactive. The labelled $^{14}CO_2$ appearing in the patient's breath was detected with a scintillation counter. ("$^{14}C$-Urea Breath Analysis, a Non-Invasive Test for *Campylobacter Pylori* in the Stomach", The Lancet, June 13, 1987, p. 1367). Bell et al pointed out that the scintillation counter required for their $^{14}C$ breath test is inexpensive and readily available, but it is by no means cheap. More important, both diagnostician and patient will obviously be uncomfortable with the thought of ingesting radioactive material, even in low radioactivity doses; and, indeed, Evans et al, supra, while pointing out the need for a simple and reliable noninvasive test, expressly mention "the undesirable radiation exposure associated with the use of $^{14}C$-urea". A breath test certainly offers the possibility of a comfortable noninvasive diagnosis, but heretofore it has clearly not been obvious to those skilled in the art how a reliable breath test can be made without requiring the ingestion of urea containing a labelled element—which is therefore relatively expensive in itself—and without the need for expensive apparatus for detecting the labelled element.

Underlying the present invention is the known fact that the local production of ammonia after ingestion of urea is a reliable indication of the presence of *C. pylori*. The invention proceeds from the theory that at least some portion of the generated ammonia is absorbed into the blood stream, passes through the liver without being broken down there, and is delivered to expired air at the alveoli of the lungs. On this basis, detection of trace amounts of ammonia in expired alveolar air would afford the possibility of a simple and inexpensive noninvasive test for *C. pylori*.

However, ammonia cannot be detected in expired alveolar air with the conventional apparatus that it is obvious to employ for the purpose. This fact has heretofore tended to cast doubt upon the underlying theory of this invention, especially when taken with the fact that the liver effects a substantial detoxification of blood passing through it and might therefore be assumed to remove ammonia from the bloodstream.

However, the applicant has discovered that it is not because of the absence of ammonia that no ammonia has heretofore been detected in the breath samples of confirmed gastritis and duodenitis patients challenged with urea, but because of the instability of ammonia in expired alveolar air. This instability is due to the relatively large quantities of water vapor and carbon dioxide in that air.

Immediately upon being expired, the breath is a mixture of gases that is at or near body temperature, having a water vapor content that is at the saturation value for that temperature. Any surface that is to be contacted by those breath gases for the purposes of ammonia detection is almost necessarily at a lower temperature. On any such surface, therefore, some condensation of the $H_2O$ content takes place. Because ammonia is readily soluble in water, the condensate water droplets tend to absorb the ammonia, and the $CO_2$ reacts with the ammonia solution to form ammonium bicarbonate, which is for practical purposes removed from the air. Owing to inevitable delay between the time of exhalation and the instant when the breath sample is presented to the ammonia detection means, the amount of gaseous ammonia in the breath sample, which was only a trace quantity in the first place, is reduced to a virtually undetectable level.

SUMMARY OF THE INVENTION

The general object of the present invention is to provide a simple, reliable and inexpensive method and means for noninvasively testing for the presence of *C. pylori*, requiring only the ingestion of ordinary urea by the patient as a preliminary to the diagnostic test, followed by collection and testing of a sample of expired alveolar air from the patient to determine whether or not ammonia is present in it.

From what has been said above, it will be apparent that a more specific but very important object of the invention is to provide a method and means for collecting and testing a breath sample in such a manner that any ammonia gas present in the sample will be maintained in the gaseous state, substantially unaffected by the $H_2O$ and $CO_2$ contents of the breath sample, so that presence of the ammonia can be ascertained with the use of generally conventional ammonia detection means.

A further specific object of the invention is to provide, in apparatus for collecting an expired breath sample that is capable of being readily tested for the presence of trace quantities of ammonia, desiccating means for removing at least a substantially major portion of the $H_2O$ content of the expired breath while substantially preventing absorption of the ammonia by such of the removed $H_2O$ as condenses and also substantially preventing reaction of the ammonia with the $CO_2$ content of the breath.

Another specific but very important object of the invention is to provide a noninvasive diagnostic test for *C. pylori*, not requiring the patient to ingest a relatively expensive urea containing a labelled element but, instead, capable of being performed after the patient has ingested a small quantity (typically 2 gms) of ordinary urea, which is a nontoxic naturally occurring component of meats and other foods.

It is also a specific object of the invention to provide for a simple and reliable test of the above described character, suitable for being performed by relatively unskilled personnel, employing an inexpensive, commercially available ammonia detector which signals its exposure to trace quantities of ammonia gas by changing color and which also provides an easily interpreted indication of the relative quantity of ammonia to which it has been exposed.

These and other objects of the invention that will appear as the description proceeds are achieved with the method of this invention, which is performed after the patient has ingested a quantity of ordinary urea and preferably during the period of about 10 to 60 minutes after such ingestion. For the purposes of the method, the patient exhales in a normal manner. The breath expired during the initial phase of the exhalation is discarded, while that expired during the remainder of the exhalation, which constitutes alveolar air, is retained as a breath sample. A characterizing feature of the method is that at least the breath sample, as it is exhaled, is passed over a body of desiccant material that is in a form to define a network of small air passages cooperating to provide the material with a relatively large surface area per unit of its volume and comprising a hygroscopic alkali that forms, with condensed water vapor absorbed from the expired breath, a solution which is more actively alkaline than ammonia and which therefore does not react with ammonia, so that the exhaled breath passed through said desiccant material comprises a dehydrated breath sample that is substantially free of water vapor but is not reduced in its ammonia concentration. The dehydrated breath sample is delivered to detector means responsive to the presence in that breath sample of trace quantities of ammonia.

Preferably the body of desiccant material comprises some form of solid-state sodium hydroxide.

Apparatus for performing the method is characterized by a duct having an input end and an output end and having a mouthpiece at its input end through which a patient exhales breath for passage through the duct. In the duct is a body of desiccant material of the previously described character. The duct has means at its outlet end for delivering a dehydrated breath sample to a detector means.

Other characteristics of a preferred form of the apparatus will appear as the description proceeds.

BRIEF DESCRIPTION OF THE DRAWINGS

In the accompanying drawings, which illustrate what is now considered a preferred embodiment of the apparatus of this invention, suited for practicing the method of the invention.

DETAILED DISCLOSURE OF PREFERRED EMBODIMENT OF THE INVENTION

Figure 1:
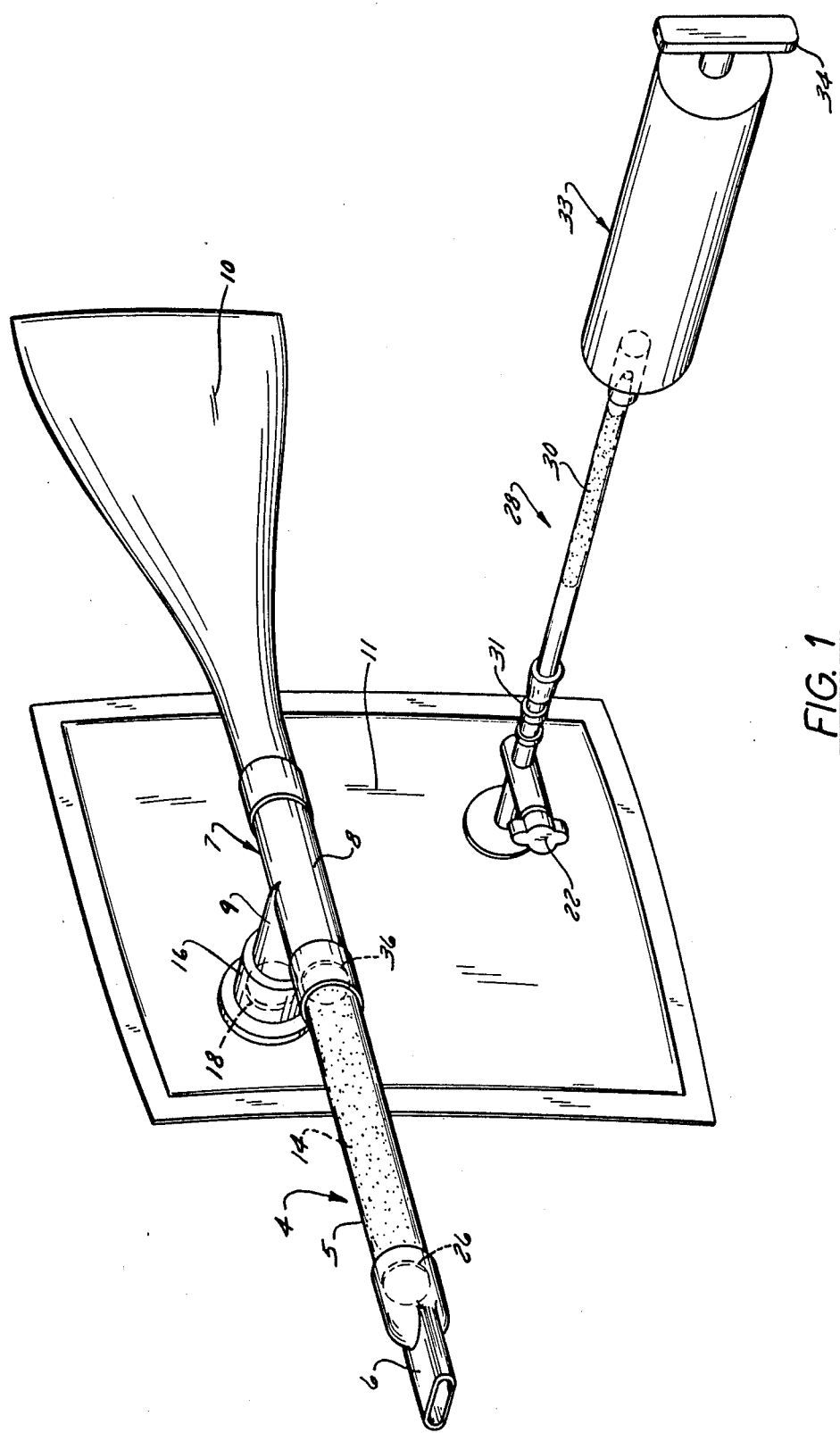
FIG. 1 is a perspective view of the assembled apparatus.
Figure 2:
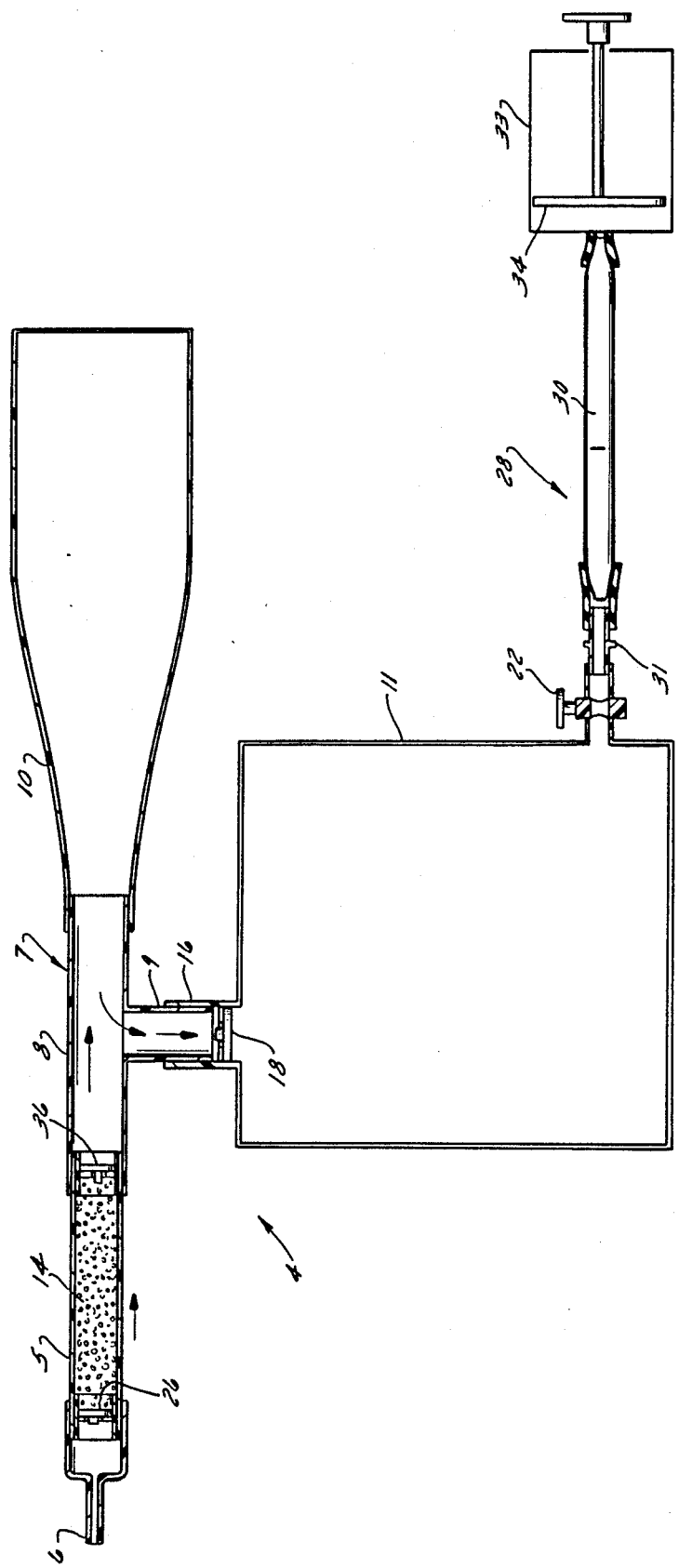
FIG. 2 is a more or less diagrammatic view of the apparatus in longitudinal section.

Breath sample collection apparatus 4 for practicing the present invention comprises, in general, an elongated duct 5, a mouthpiece 6 connected to an inlet end of the duct, a tee fitting 7 having a straight-through leg 8 that is connected to the outlet end of the duct 5 and having a branch leg 9, a waste bag 10 for connection to the straight-through leg 8 of the tee fitting 7, and a storage bag 11 for connection to the branch leg 9 of the tee fitting. The connections of the mouthpiece 6 and the tee fitting 7 to the duct 5 are preferably readily detachable, as are the connections of the bags 10 and 11 to the tee fitting.

The apparatus 4 is used to collect a dehydrated sample of a patient's expired alveolar air. For that purpose the patient places the mouthpiece 6 against his or her lips and exhales into it in a normal manner. Inside the duct 5, extending along most of its length, there is a body 14 of preferably solid-state desiccant material that is described hereinafter. As the exhaled air flows along the duct 5 from the mouthpiece 6 to the tee fitting 7, the desiccant material serves to remove substantially all of the water vapor content of the breath and converts it to an alkaline solution, to prevent loss of the ammonia gas content of the breath.

In the inlet end portion of the duct 5, interposed between the body 14 of desiccant material and the mouthpiece 6, there is a check valve 26 that is arranged to permit airflow through the duct in the direction from the mouthpiece 6 towards the tee fitting 7 but to prevent airflow in the opposite direction. Permanently and sealingly connected to the storage bag 11 is a nipple-like inlet fitting 16 that provides for detachable connection of the storage bag to the branch leg 9 of the tee fitting. Inside this nipple fitting 16 is another check valve 18, which can be identical with the check valve 26 and which is arranged to permit flow into the storage bag 11 but prevent flow out of it. Also permanently sealed to the storage bag, at a location on it that is suitably spaced from the inlet fitting 16, is a small manually operable valve or stopcock 22 that can be closed for cooperation with the check valve 18 in preventing escape of air from the storage bag and can be opened to permit withdrawal of air from that bag.

During an initial phase of a patient's exhalation into the mouthpiece 6, the expired air flows all the way through the straight-through leg 8 of the tee fitting and into the waste bag 10. This flow into the waste bag 10, in preference to flow into the storage bag 11, is constrained by the geometry of the tee fitting (which then functions as a venturi) in cooperation with the check valve 18 at the storage bag inlet.

The waste bag 10, which is made of Pliofilm or similar supple, inexpensive and air-tight material, is initially in fully collapsed condition and has a predetermined capacity such that it is brought to full inflation by all of the "dead space" air exhaled by the patient, plus a small amount of alveolar air. By "dead space" air is meant the air that issues from the oral cavity, the nose, the trachea and the bronchi during the initial phase of exhalation, and which is for the most part atmospheric air, as distinguished from the alveolar air that is expired during the last portion of a normal exhalation. The "dead space" air is of no value for purposes of the diagnostic test of the present invention and is collected in the waste bag 10 for separation from the alveolar air that is useful for diagnosis.

It will be apparent that when the waste bag 10 is fully inflated, the pressure in the straight-through leg 8 of the tee fitting will rise as the exhalation continues, and in response to this increased pressure the valve 18 will open, permitting all of the remainder of the exhaled breath to pass through the branch leg 9 and thus into the storage bag 11.

After a complete exhalation the waste bag is filled to capacity with "dead space" air while the storage bag 11 contains a usefully large quantity of dehydrated alveolar air. The storage bag is made of supple, air-tight material such as laminated metal foil, and therefore the dehydrated alveolar air sample remains in it for a substantially long period of time and until it is withdrawn through the stopcock 22. It will be understood that the waste bag 10 can be removed from the tee fitting at any convenient time after the patient has exhaled into the collection apparatus 4 and can then be collapsed and reattached for subsequent use. The check valve 26 near the mouthpiece 6 serves to prevent any contaminants that may be present in the waste bag, from breath residues or other sources, from being carried back to a patient using the apparatus 4, and therefore the waste bag 10 can be reused repeatedly.

Detector apparatus 28 for use with the collection apparatus 4 comprises, in this case, an indicating sensor 30, an adaptor fitting 31 that provides for detachable but sealed coupling of the sensor to the outlet of the storage bag stopcock 22, and a syringe or small pump 33 that can be detachably connected to the sensor for drawing through the sensor a predetermined volume of dehydrated alveolar air from the storage bag.

The sensor 30 can be an electrode device of known type, cooperating with suitable electronic circuitry and readout means, or it can comprise a glass tube filled with an alkali-indicating material, e.g., granules of substantially inert material coated with cresol red. The presently preferred indicating sensor 30 is a commercially available non-reusable device that is ammonia-specific, made in Japan by Gastec and sold in the United States by Sensidyne, Inc. of Clearwater, Fla. under its catalog designation 3L. It comprises a slender glass tube having an integral seal at each of its ends, filled with a granular material that changes color as ammonia is passed through it. The seals are broken off of the ends of this sensor tube 30 just before it is connected to the adaptor fitting 31 and to the syringe 33, to permit flow of air through it. An appropriate marking on the tube designates its inlet end, which is connected with the stopcock by means of the adaptor fitting 31.

The presently preferred pump or syringe 33 is a manually operable Sensidyne/Gastec plunger pump, also available from Sensidyne, Inc., that is particularly designed for cooperation with the preferred indicating sensors. This syringe 33 has a plunger 34 that can be drawn outward through adjustably predeterminable strokes to enable predetermined quantities of air (for example, 50 ml and 100 ml) to be drawn into it. Thus, with the storage bag 11, the indicating sensor 30 and the syringe 33 connected as described above, the stopcock 22 is opened and the plunger 34 of the syringe is pulled out to an adjusted stop to cause a predetermined quantity of the breath sample in the storage bag to be drawn through the tube of the sensor 30. If the air drawn through the sensor 30 contains ammonia, a color change moves along the tube at a rate proportional to the amount of ammonia passing through it.

There are calibration marks at regular intervals along the length of the sensor tube 30, for quantitative evaluation of the ammonia content of the gas drawn through it. Normally a breath sample is tested with a single stroke of the plunger 34 to draw through the sensor 30 a predetermined quantity of dehydrated alveolar air, which quantity is preferably uniform from sample to sample so that the length of the color change zone at the conclusion of a syringe plunger stoke will always be proportional to the ppm of ammonia in the sampled air and the results of successive tests can be directly and meaningfully compared with one another. The preferred indicating sensor has a sensitivity of 1-30 ppm.

For convenience in use of the detector apparatus 28, the storage bag 11 can be detached from the tee fitting 7 of the collector apparatus 4 at any time after the breath sample is obtained, since the check valve 18 in the storage bag inlet fitting 16 prevents leakage of the sample out of the storage bag. It will be apparent that no great degree of skill is needed for assembling the apparatus to collect a breath sample, for taking and testing the sample, and for reading the results signified by the color change zone on the indicating sensor.

Returning now to a consideration of the collection apparatus 4, an essential element of it is the body 14 of desiccant material in the duct 5. This material is relied upon to remove substantially all of the water vapor from the breath sample collected in the storage bag 11, and it thus prevents loss of the gaseous ammonia in that sample, even if the sample is stored for a relatively long time before being tested. The material must be hygroscopic and alkaline, should form with water a solution more actively alkaline than ammonia, and should be in such form as to define a network of small passages in which expired breath flows in contact with the material and which cooperate to provide the material with a large surface area per unit of its gross volume. In flowing through such a network of passages the expired air is gently agitated to bring all portions of it into contact with the material. Because the material is hygroscopic, it strips substantially the entire water vapor content out of expired breath passing through it, so that such air is dehydrated when it reaches the tee fitting 7. Because the desiccant material is alkaline, it prevents ammonia from dissolving in the condensate, and discourages combination of the $CO_2$ and $H_2O$ contents of the expired breath with ammonia that is in the sample.

Conceivably the desiccant material could be a liquid that is hygroscopic and alkaline, so that the necessary network of passageways would be formed by the breath bubbling through it. Obviously, however, such a liquid could not be an aqueous solution, since its water content would tend to moisten the breath sample and thus defeat the purpose of employing a desiccant.

Ordinarily, therefore, a solid-state desiccant will be preferred. The desiccant material should be one that is granular or particulate, to provide the necessary network of passages. Lithium hydroxide may be a suitable material. However, the presently preferred desiccant material comprises anhydrous sodium hydroxide (NaOH). This can be in the form of pellets of pure anhydrous sodium hydroxide, but such pellets have been found to be somewhat difficult to handle because of their tendency to become sticky as they absorb water vapor from the atmosphere, although they are otherwise entirely satisfactory.

The most desirable form of desiccant material now known to the applicant is sold under the trade name ASCARITE by Thomas Scientific of Swedesboro, N.J. It consists of silica (sand) carrier particles that are coated with anydrous sodium hydroxide.

The ASCARITE granules have the desirable property of undergoing a noticeable change in color upon absorbing water, thus giving a visual signal when the hygroscopic property of the material has been depleted and the spent material should be replaced. So that this color change can be readily visible, the duct 5 is preferably transparent.

Although the desiccant material is toxic, the patient and other persons are protected from contact with it by the check valve 18, which prevents the material from being drawn towards the patient's mouth even if the patient should attempt to inhale vigorously through the mouthpiece 6. Another similar check valve 36 can be inserted into the duct 5 near its outlet end to cooperate with the inlet check valve 18 in preventing spillage of the desiccant material out of the duct, or a fine-mesh screen (not shown) can be installed in that location.

The apparatus of this invention will usually be used to make a so-called base-line test of a sample of the patient's breath that is taken before the patient has ingested any urea, for purposes of comparison with a breath sample taken after a suitable interval following the patient's ingestion of urea. A suitable amount of urea to be ingested for purposes of the test is 2 gms, but this amount is by no means critical, although a standardized quantity would seem to be desirable in the interests of facilitating comparison of results of tests made at different times on a particular patient and of results of tests made on different patients.

From the foregoing description taken with the accompanying drawings it will be apparent that this invention provides a simple and inexpensive method and means for performing a reliable diagnostic test for ascertaining the presence of *C. pylori* in the stomach or duodenum, said test being noninvasive, reliable, and capable of being performed by relatively unskilled personnel without discomfort to the patient.

What is claimed is:

1. A method of noninvasive testing for presence of *Campylobacter pylori* in the gastroenteral tract of a patient, characterized by the steps of:
   A. ingestion by the patient of a quantity of urea;
   B. after an interval of not substantially less than 10 minutes following ingestion of urea, production by the patient of a sample of expired alveolar air by exhalation;
   C. directing the expired alveolar air, as it issues from the patient, to flow past and in intimate contact with breath dehydration means for removing water from said expired air but preserving ammonia that may be present therein, comprising a desiccant body to alkaline hygroscopic material, and thus producing a dehydrated alveolar air sample with and an unchanged ammonia content; and
   D. conducting at least a portion of the dehydrated alveolar air sample into contact with a sensor and producing with the sensor a perceptible signal in response to the presence of ammonia in that sample.

2. The method of claim 1, further characterized by:
   (1) so directing all of the breath expired by the patient during one exhalation as to cause it to flow in intimate contact with said breath dehydration means; and
   (2) producing said dehydrated alveolar air sample by
      (a) discarding all breath expired by the patient during an initial portion of said one exhalation that continues from the beginning thereof to a time when only alveolar air is being expired, and
      (b) collecting for passage into contact with said sensor the breath expired during the remainder of said one exhalation following said initial period.

3. Apparatus for collecting a breath sample for noninvasive testing to detect the presence of *Campylobacter pylori* in the gastroenteral tract of a patient who has ingested a quantity of urea, said apparatus being characterized by:
   A. a duct
      (1) having an inlet end and an outlet end and
      (2) having means at said inlet end for enabling the patient to direct expired breath through said duct;
   B. a body of desiccant material in said duct, said desiccant material
      (1) defining a network of small air passages that cooperate to provide the material with a large surface area per unit of its gross volume and
      (2) comprising a hygroscopic alkaline means for removing water while remaining inert to ammonia that may also be present,
      so that exhaled breath which has passed through said desiccant material comprises a dehydrated breath sample that is substantially free of water vapor; and
   C. means at the outlet end of said duct to provide for delivery of the dehydrated breath sample to detector means responsive to presence in that breath sample of trace quantities of ammonia.

4. The apparatus of claim 3, further characterized in that said body of desiccant material comprises solid-state sodium hydroxide.

5. The apparatus of claim 3, further characterized in that: said body of desiccant material
   (1) is in solid-state granular form and
   (2) comprises sodium hydroxide.

6. The apparatus of claim 5, further characterized by:
   (1) check valve means in said duct, adjacent to one of said ends thereof, arranged to permit passage of air through the duct in a forward direction from its said inlet end to its said outlet end and to prevent passage of air in the opposite direction, and
   (2) means at the other end of said duct cooperating with said check valve means to prevent escape of desiccant material from the duct but permitting flow of air through the duct in said forward direction.

7. A method of noninvasive testing for the presence of *Campylobacter pylori* in the gastroenteral tract of a patient, characterized by the steps of:
   A. ingestion by the patient of a quantity of urea;
   B. after an interval of not substantially less than 10 minutes following ingestion of urea, production by the patient of a sample of expired alveolar air by exhalation;
   C. directing the expired alveolar air, as it issues from the patient, to flow to a desiccant body of solid state sodium hydroxide that defines numerous small air passages, and to flow through said air passages in intimate contact with the sodium hydroxide, and thus producing a dehydrated alveolar air sample with an unchanged ammonia content; and
   D. conducting at least a portion of the dehydrated alveolar air sample into contact with a sensor and producing with the sensor a perceptible signal in response to the presence of ammonia in that sample.

8. A subassembly adapted for incorporation in breath collection apparatus of the type comprising a mouthpiece into which a patient exhales to provide a breath sample, a storage bag in which the breath sample is collected and which has an inlet fitting for connection with said mouthpiece, an inlet valve associated with said inlet fitting through which exhaled breath is permitted to enter the storage bag but whereby escape of air from that bag is prevented, and an outlet fitting comprising a further valve that provides for controlled withdrawal of air from the storage bag for delivery to a sensor, said subassembly providing for the preservation of ammonia that may be present in air exhaled by the patient and collected in the storage bag and being characterized by:
   A. a duct for directing exhaled breath from the mouthpiece towards said storage bag,
      (1) said duct having an inlet end at which said mouthpiece is connectable and
      (2) having an opposite outlet end that is connectable with said inlet fitting;
   B. a body of solid state desiccant material in said duct, said desiccant material
      (1) defining a network of small air passages that cooperate to provide the material with a large surface area per unit of its gross volume and
      (2) comprising hygroscopic alkaline means for removing water without reacting with any ammonia that may be present,
      so that exhaled breath which has passed through said desiccant material in flow towards the storage bag comprises a dehydrated breath sample that is substantially free from water vapor;
   C. check valve means in said duct, near one of said ends thereof, permitting flow of air through the duct in a forward direction from its inlet end towards its outlet end but preventing flow of air therethrough in the opposite direction; and
   D. means in said duct, near the other of said ends thereof, cooperating with said check valve means for confining said body of material in the duct and permitting flow of air through the duct in said forward direction.

9. The subassembly of claim 8, further characterized in that said body of material comprises granules of a material that is essentially inert to water, carbon dioxide and ammonia, coated with sodium hydroxide.

* * * * *